United States Patent
Brown et al.

(10) Patent No.: US 10,398,812 B2
(45) Date of Patent: Sep. 3, 2019

(54) TUBE STRIPPING DEVICE

(71) Applicants: Diana S. Brown, Salem, OH (US); Richard Madjarac, Salem, OH (US)

(72) Inventors: Diana S. Brown, Salem, OH (US); Richard Madjarac, Salem, OH (US)

(*) Notice: Subject to any disclaimer, the term of this patent is extended or adjusted under 35 U.S.C. 154(b) by 0 days.

(21) Appl. No.: 16/027,794

(22) Filed: Jul. 5, 2018

(65) Prior Publication Data

US 2019/0009011 A1 Jan. 10, 2019

Related U.S. Application Data

(60) Provisional application No. 62/528,736, filed on Jul. 5, 2017.

(51) Int. Cl.
| | |
|---|---|
| *A61M 1/00* | (2006.01) |
| *B08B 1/04* | (2006.01) |
| *B08B 9/027* | (2006.01) |
| *B08B 9/023* | (2006.01) |
| *B08B 7/02* | (2006.01) |

(52) U.S. Cl.
CPC ............ *A61M 1/0078* (2013.01); *B08B 1/04* (2013.01); *B08B 9/023* (2013.01); *B08B 9/027* (2013.01); *A61M 2209/10* (2013.01); *B08B 7/02* (2013.01); *B08B 2209/027* (2013.01)

(58) Field of Classification Search
CPC ... A61M 1/0078; A61M 2209/10; B08B 1/04; B08B 9/027; B08B 9/023; B08B 7/20; B08B 2209/027
USPC .................. 222/201, 202; 606/209, 205–211
See application file for complete search history.

(56) References Cited

U.S. PATENT DOCUMENTS

| | | | |
|---|---|---|---|
| 1,699,993 A | * | 1/1929 | Rosensteel .......... A61M 1/0078 15/1 |
| 3,194,452 A | | 7/1965 | Sanderford |
| 3,847,370 A | * | 11/1974 | Engelsher ........... A61M 1/0078 222/214 |
| 5,141,503 A | | 8/1992 | Sewell, Jr. |
| 5,630,821 A | * | 5/1997 | Klaas .................... A61F 2/1664 606/107 |
| 5,881,916 A | | 3/1999 | Madjarac |
| 7,998,168 B2 | | 8/2011 | Kleimann, Sr. |

(Continued)

OTHER PUBLICATIONS

Tube Evac http://tubeevac.com, Tube-Evac Device, Aug. 2012, United States.

*Primary Examiner* — Lien M Ngo
(74) *Attorney, Agent, or Firm* — Jacob M. Ward; Ward Law Office LLC (57) ABSTRACT

A tube stripping device includes a main body and a pair of free rotating rollers. The main body has a first arm, a second arm, and a spring portion. The first arm and the second arm extend outwardly from the spring portion. The first arm and the second arm are manually movable relative to each other from a spaced apart default position to a stripping position. The spring portion normally biases the first arm and the second arm apart and to the default position. The first roller is rotatably disposed at a first free end of the first arm, and the second roller rotatably disposed on a second free end of the second arm. The first roller is oriented generally parallel with the second roller. The first roller has an uninterrupted outer circumferential surface, and the second roller has an outer circumferential surface with a groove formed therein.

19 Claims, 6 Drawing Sheets

(56) References Cited

U.S. PATENT DOCUMENTS

| | | | | |
|---|---|---|---|---|
| 8,287,654 | B2* | 10/2012 | Shaffer | A61M 25/00 134/16 |
| 2003/0218105 | A1* | 11/2003 | Sones | A61J 9/0692 248/104 |
| 2006/0196995 | A1* | 9/2006 | Mori | A47B 21/06 248/74.2 |
| 2009/0120957 | A1* | 5/2009 | Phillips | A61M 1/0078 222/102 |
| 2010/0294378 | A1* | 11/2010 | Kleinnann, Sr. | B08B 9/027 137/15.04 |
| 2011/0314977 | A1* | 12/2011 | Lewis | A61M 39/284 81/486 |
| 2013/0110087 | A1* | 5/2013 | Kane | A61M 25/00 604/543 |

* cited by examiner

TUBE STRIPPING DEVICE

CROSS-REFERENCE TO RELATED APPLICATIONS

This application claims the benefit of U.S. Provisional Application No. 62/528,736, filed on Jul. 5, 2017. The entire disclosure of the above application is hereby incorporated herein by reference.

FIELD

The present disclosure relates to a medical device and, more particularly, to a device for stripping or cleaning tubes.

BACKGROUND

Hospital infections pose a serious risk to patients. To reduce the risk of infection, hospital wings are constantly sterilized. However, there are items that remain difficult to clean, especially medical tubes such as surgical drainage tubes. Surgical drainage tubes are very difficult to clean, and debris can build up quickly and cause an infection. Consequently, there is a need for a device that cleans the interior of medical tubes, thereby lowering the rates of infection.

Known devices for cleaning tubes are described in, for example, U.S. Pat. No. 3,194,452 to Sanderford. The Sanderford patent relates to a hand-held instrument pivotally connected at one end with rollers, and adapted at the other end to squeeze tubing between the rollers to clean the interior portion of the tubing. The Sanderford patent shows an in-line stripping of the tubing by the instrument.

Furthermore, U.S. Pat. No. 5,141,503 to Sewell, Jr. describes a wound drainage catheter with an aperture and a closed reservoir system. The wound draining catheter has of the Sewell, Jr. patent has a plug and a thread for pulling the plug through the tubing or lumen, in order to clear the catheter of occluded material.

Another known tube unclogging device is described in U.S. Pat. No. 5,881,916 to Madjarac. The Madjarac patent describes an instrument comprising in combination a U-shaped body having a pair of cylindrical rollers mounted for rotation on each end of the opened end of the U-shaped body, said rollers being oriented parallel to each other and to the sides of the U-shaped body, spaced apart and in relationship for movement into and out of engagement with opposite sides of the tubing.

A further known drain tube stripper is described in U.S. Pat. No. 7,998,168 to Kleimann, Sr. The Kleimann, Sr. patent describes a drain tube stripper containing two handles pivotally joined at one end. The second end of each handle contains a roller. The rollers meet when the handles are pressed together. The handles are of unequal length. A drain tube, e.g., surgical drain, can be stripped of fluid and material buildup by placing the open rollers over the tube and pressing the handles together. The rollers thereby pinch the drain tube and the rollers allow the device to be moved along the drain tube pushing fluid and material ahead of the rollers. The drain tube stripper allows the tube to enter between the rollers from the side and exit from the side of the opposing handle. The tube drain stripper may also contain a guide component to minimize entanglement of the drain and the device is rolled along the drain tubing.

These known tube stripping devices are complicated, and are prone to breakage and an undesirable seizing up of the rollers in use. These known devices are also time consuming and unwieldy to use. The use of in-line tube stripping too, where the stripping motion is parallel with the orientation of the user's hand conducting the stripping, is further believed to undesirably increase the opportunity for contamination and spread of infection.

There is a continuing need for a tube stripping device that cleans medical tubing quickly and effectively. Desirably, the tube stripping device is simple to use and minimizes a risk of infection in operation.

SUMMARY

In concordance with the instant disclosure, a tube stripping device that cleans medical tubing quickly and effectively, and which is simple to use and minimizes a risk of infection in operation, has been surprisingly discovered.

In one embodiment, a tube stripping device has a main body with a closed end and an opened end. The main body further has a first arm, a second arm, and a spring portion. The first arm and the second arm are connected to and extend outwardly from the spring portion of the main body. The first arm and the second arm are also selectively and manually movable relative to each other, particularly from a spaced apart default position to a stripping position. The spring portion normally biases the first arm and the second arm apart and to the default position, where the arms are not being manually moved to stripping position. The tube stripping device further has a pair of free rotating rollers including a first roller and a second roller. The first roller is rotatably disposed on a first free end of the first arm. The second roller is rotatably disposed on a second free end of the second arm. The first roller is oriented generally parallel with the second roller. The first roller also has an uninterrupted outer circumferential surface. The second roller has an interrupted outer circumferential surface with a groove formed therein.

In another embodiment, the first roller is oriented on a first axis and a major portion of the first arm is oriented on a second axis. The first axis is transverse to the second axis and together the first and second axes define an obtuse angle. In particular, the obtuse angle is between 90° and 130°. The pair of fasteners may further include a first fastener disposed at the first free end of the first arm and a second fastener disposed at the second free end of the second arm. The fasteners may be removably disposed, for example, via a threaded cooperation with the free ends, to permit for a rapid replacement of the first and second rollers. Further, the main body may have a polymeric (e.g., rubberized) coating disposed on each of the first arm and the second arm, to facilitate gripping of the main body. The polymeric coating is further disposed on the spring portion of the main body but not disposed on the first free end of the first arm and the second free end of the second arm where the rollers are disposed, so as to not interfere with the free rolling characteristics of the rollers.

In a further embodiment, a distance between the first fastener and a bend in the main body defining a transition between a major portion of the first arm and the first free end is greater than a length of the first roller. Likewise, a distance between the second fastener and a bend in the main body defining a transition between a major portion of the second arm and the second free end is greater than a length of the second roller. This creates a gap in operation that militates against a seizing up of the rollers, and otherwise facilitates the free rolling characteristics of the rollers. The first fastener is also removably attached to the first free end and the second fastener is removably attached to the second free end. This permits for an easy manual replacement of the first roller and the second roller. In particular, each of the first free end of the first arm and the second free end of the second arm may have external threads, and each of the first fastener and the second fastener may have internal threads. The external threads cooperate with the internal threads to selectively secure the first fastener to the first free end and the second fastener to the second free end.

In yet another embodiment, the apparatus is a tube stripping device used for clearing and dislodging the contents of wound drainage tubes, catheters, chest tubing, common duct T tubing, intravenous (IV) tubing and other deformable tubing. The device has a substantially U-shaped body with a pair of rollers disposed at the opened end of the U-shaped body. The rollers are periodically squeezed together by the operator and rolled along the drainage tube to keep the tube clear and unclogged. The rollers contain a central groove to secure the drainage tube between the rollers. The tube stripping device is simple and inexpensive in its construction, and can be made from a plastic, metal, or other suitable material as chosen by a skilled artisan. In addition, the device may be used by the patient without the assistance of another party such as a nurse or physician in unclogging a tube inserted into the patient, particularly following surgery.

It should be appreciated that the rollers may be interchangeable to correspond with the size of tubing required to be cleaned. The user of the present device may insert rollers of varying sizes corresponding to different sized tubing, and thus it is unnecessary to have a separate device for each size of tubing in operation. Additionally, the U-shaped body can have a clamp inter-disposed between the rollers. The clamp can secure the U-shaped body onto the tube, so the user isn't required to squeeze the U-shaped body as the rollers are pulled along the distance of the tube.

In yet a further embodiment, the tube unclogging device is a tool is made from an approximately 12" section of wire that has been bent into a U-shape, with a pair of plastic rollers rotatably affixed to the wire. Each roller is attached to an end of the wire with fasteners that are configured to keep the rollers in position. One roller has a groove in the center that is configured to abut a tube. The groove within the roller secures the tubing in the center of the rollers for a smooth swipe. In operation, a user places the plastic tubing in-between the rollers, and squeezes the U-shaped body while sliding the rollers down the tube. The rollers will pinch the tube and drain the catheter of any excess liquid or debris.

In yet another embodiment, the construction and material of the tube unclogging device may be either a molded plastic body or a one-piece wire frame with a loop in the bottom of the handle. Rubber grippers may be added where a person squeezes the wire causing the rollers to grip the tubing. Placing the loop in the handle further removes tension on the wire allowing the wire to be squeezed with ease. The one-piece bent wire simplifies the manufacturing of the device and cuts out the need for plastic molds.

In an exemplary embodiment, a tube stripping device for cleaning resilient tubing such as wound drainage tubing, catheters, chest tubing, common duct T tubing, intravenous (IV) tubing and other deformable tubing includes, in combination, a substantially U-shaped body having a pair of cylindrical rollers mounted for rotation on each end of the opened end of the U-shaped body, the rollers being oriented parallel to each other. The user's hand can grasp the U-shaped body for moving the rollers toward each other and against the tubing while also moving the rollers along the length of the tubing. Where the user grips the U-shaped body with sufficient force, the tube may thereby be cleared of liquid and debris.

Further areas of applicability will become apparent from the description provided herein. It should be understood that the description and specific examples are intended for purposes of illustration only and are not intended to limit the scope of the present disclosure.

DRAWINGS

The above, as well as other advantages of the present invention, will become clear to those skilled in the art from the following detailed description of a preferred embodiment when considered in the light of the accompanying drawings in which.

DETAILED DESCRIPTION

The following detailed description and appended drawings describe and illustrate various embodiments of the invention. The description and drawings serve to enable one skilled in the art to make and use the invention, and are not intended to limit the scope of the invention in any manner. In respect of the methods disclosed, the steps presented are exemplary in nature, and thus, the order of the steps is not necessary or critical unless otherwise disclosed.

FIGS. 1-10 illustrate a tube stripping device 100 according to one embodiment of the disclosure. The tube stripping device 100 is used to unclog medical tubes such as wound drainage tubes, catheters, chest tubing, common duct T tubing, intravenous (IV) tubing, and other deformable tubing, as non-limiting examples. Other suitable uses for the tube stripping device 100 are also considered to be within the scope of the present disclosure.

Figure 1:
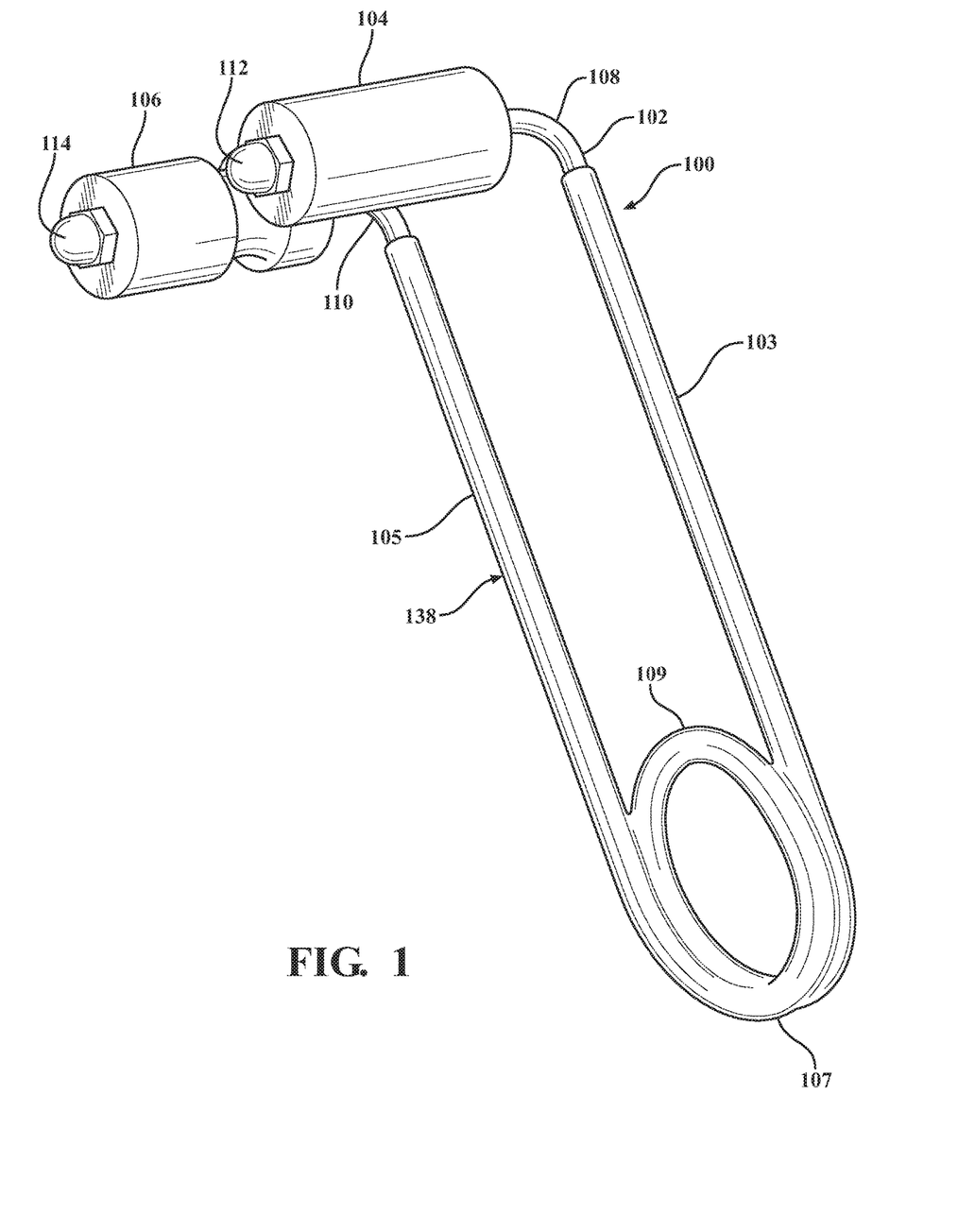
FIG. 1 is a side perspective view of a tube stripping device according to one embodiment of the disclosure.
Figure 2:
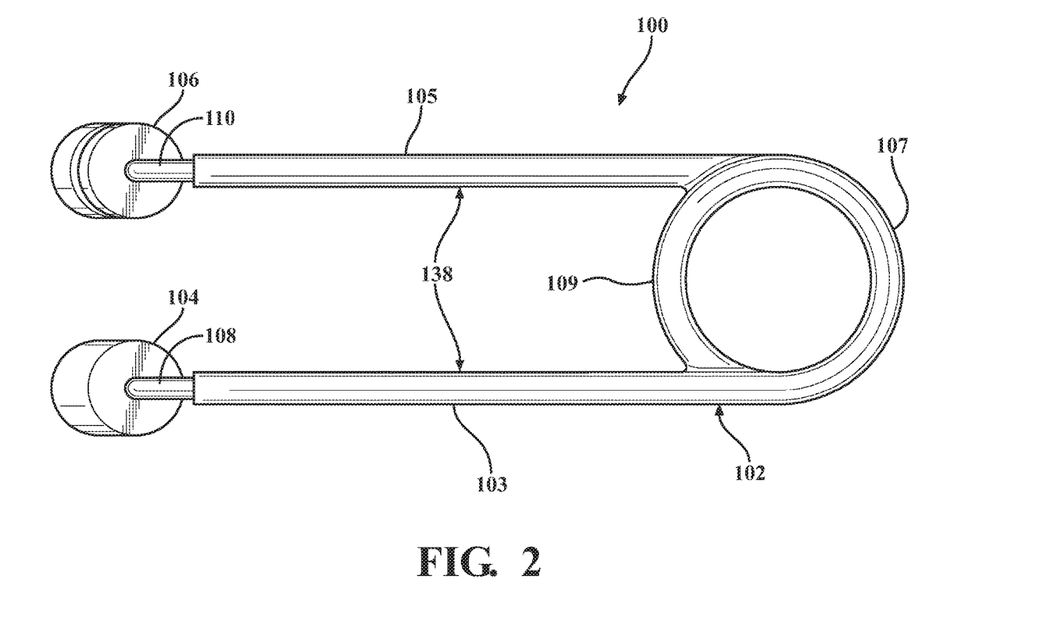
FIG. 2 is a top plan view of the tube stripping device shown in FIG. 1.
Figure 3:
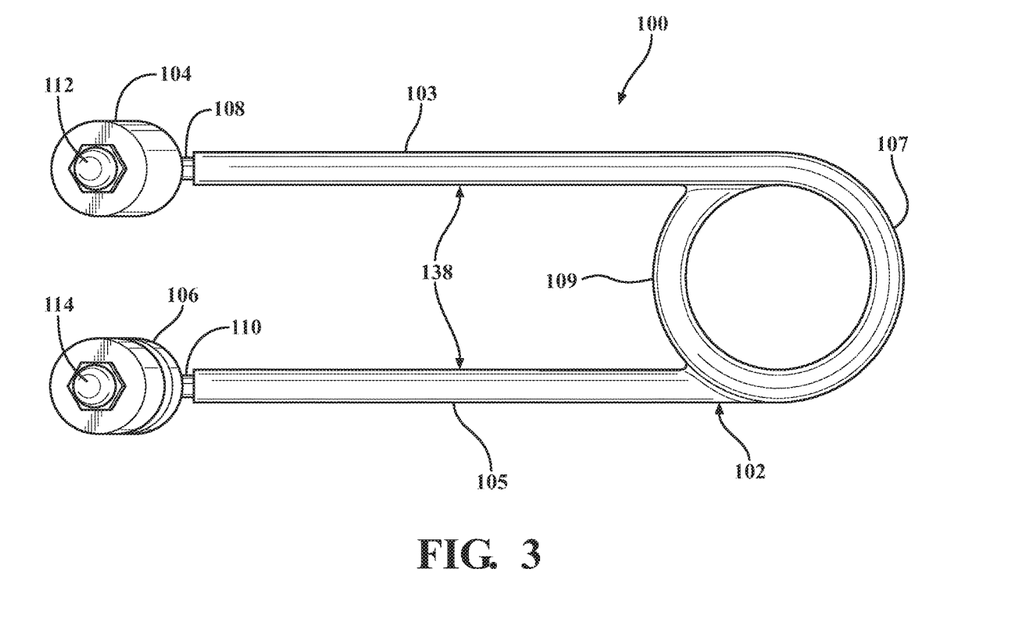
FIG. 3 is a bottom plan view of the tube stripping device shown in FIG. 1.

The tube stripping device 100 has a main body 102 with a first roller 104 and a second roller 106. The main body 102 has a first arm 103, a second arm 105, and a spring portion 107. The main body 102 further has an opened end and a closed end. The spring portion 107 connects the first arm 103 and the second arm 105 at the closed end of the main body 102. The first arm 103 and the second arm 105 extend outwardly from the spring portion 107 toward the opened end of the main body 102. The main body 102 may be substantially U- or V-shaped, as non-limiting examples. Other suitable shapes for the main body 102 may also be employed, as desired.

The main body 102 can be made medical-grade plastic or metal, as non-limiting examples. The first arm, 103, the second arm 105, and the spring portion 107 may be integrally formed as a single body, or may be separately formed as subsequently connected, as desired. Likewise, the spring portion 107 may be formed from a same or different material compared to the material of the first and second arms 103, 105. Other suitable materials for the main body 102 may also be employed within the scope of the present disclosure.

The spring portion 107 of the main body 102 permits the first arm 103 and the second arm 105 to be selectively moved toward each other to a closely adjacent stripping position, for example, when squeezed together by a user. The spring portion 107 also generally biases the first arm 103 and the second arm 105 apart, with the first arm 103 and the second arm 105 subsequently returning to a spaced apart default position, for example, when not being squeezed together by the user.

As shown in FIGS. 1-8 and 10, the spring portion 107 contains at least one coil 109. The coil 109 allows for the relative movement for the first arm 103 to the second arm 105. Although a single coil 109 is shown, one of ordinary skill in the art may select either a spring portion 107 having no coils 109, e.g., a resilient U- or V-shaped spring at the closed end of the main body 2, or additional coils 109, in order to provide for a predetermined spring force for the main body 102, as desired.

Figure 10:
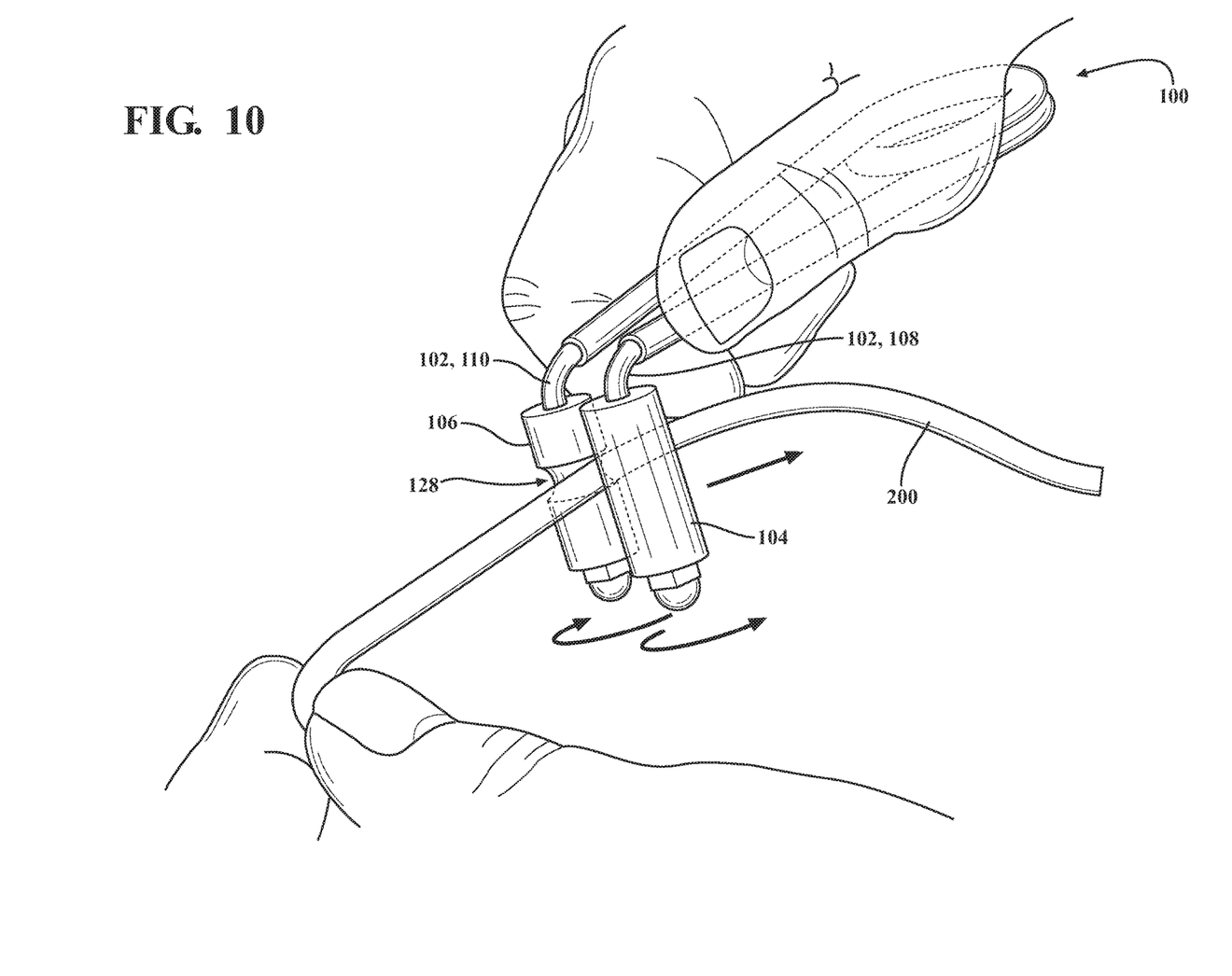
FIG. 10 is a side perspective view of the tube stripping device shown in FIG. 1, and further illustrated in use for stripping or cleaning medical tubing.

As shown in FIGS. 1-8 and 10, the first and second rollers 104, 106 are rotatably disposed at the opened end of the main body 102. In particular, the first and second rollers 104, 106 may be oriented substantially parallel to each other and configured to secure tubing 200 therebetween when in the stripping position, as shown in FIG. 10. The first and second rollers 104, 106 may be formed from medical-grade plastic or metal, as non-limiting examples. The medical grade plastic, where used, may also be compounded with lubricants or waxes which rise to the surface of the plastic and form a lubricating layer that may further serve to minimize friction between the rollers 104, 106 and the ends 108, 110 on which they are disposed. One of ordinary skill in the art may also select other suitable materials for the rollers 104, 106 within the scope of the disclosure.

Figure 4:
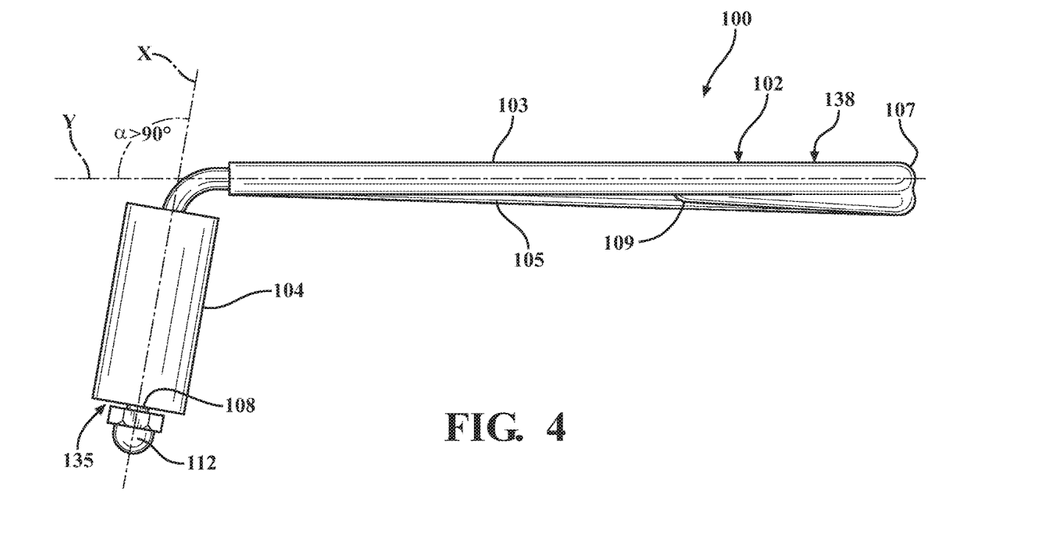
FIG. 4 is a right side elevational view of the tube stripping device shown in FIG. 1.
Figure 5:
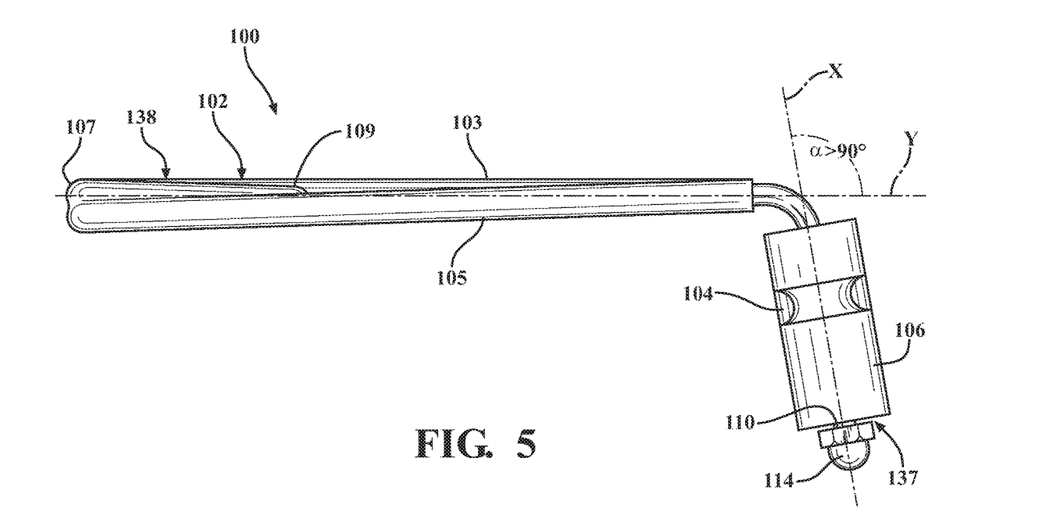
FIG. 5 is a left side elevational view of the tube stripping device shown in FIG. 1.
Figure 6:
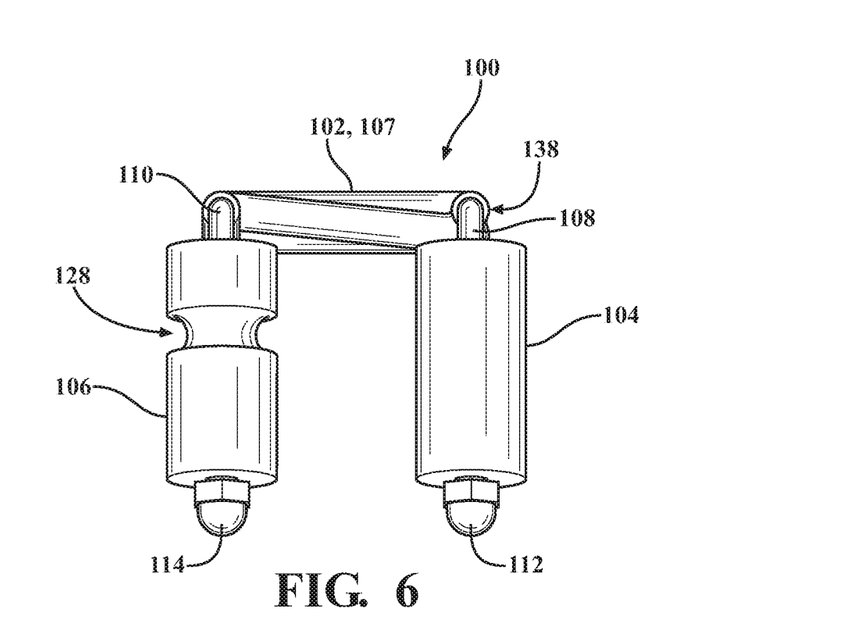
FIG. 6 is a front elevational view of the tube stripping device shown in FIG. 1.
Figure 7:
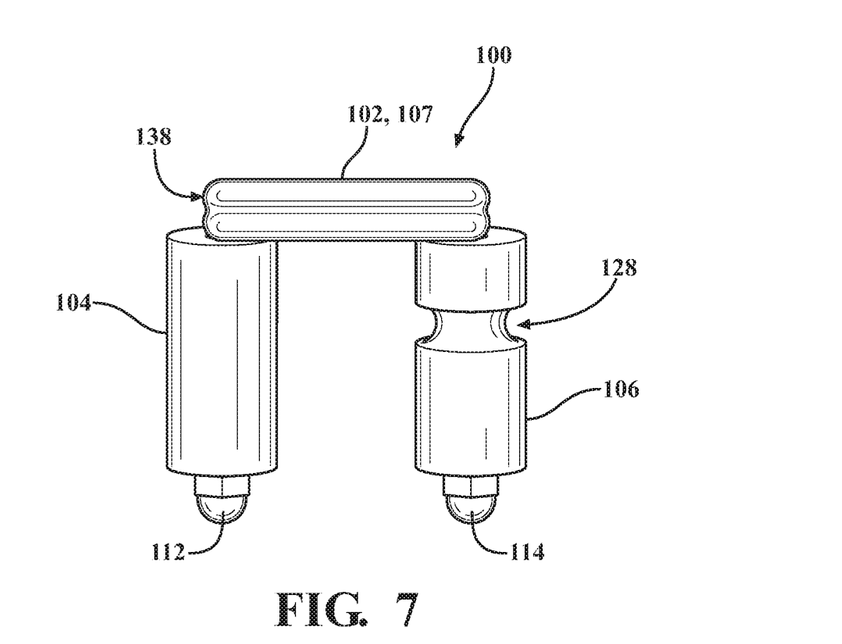
FIG. 7 is a rear elevational view of the tube stripping device shown in FIG. 1.

With reference to FIGS. 4-5, each of the first and second rollers 104, 106, and likewise the first and second free ends 108, 110, may also be also oriented on a first axis X that is transverse to a second axis Y along which the respective one of the first and second arms 105, 107 is disposed. The angle α between the first axis X and the second axis Y is obtuse, for example, greater than 90°, more particularly between 90° and 130°, and most particularly about 110°, as non-limiting examples. In order to provide the obtuse angle α, free ends 108, 110 of the arms 103, 105 may be bent at the desired angle.

Advantageously, it should also be appreciated that the obtuse angle α permits for the stripping of the tubing 200 while maintaining the hand of the user operating the tube stripping device 100 off to the side and out of the way of the tubing 200. One of ordinary skill in the art will further understand that this results in a more hygienic use of the tube stripping device 100 in operation, and minimizes an opportunity for spread of infection.

With renewed reference to FIGS. 1, 3, 6-8, and 10, each of the first roller 104 and the second roller 106 may further be secured to the main body body 2 using a first fastener 112 and a second fastener 114, respectively. The first and second fasteners 112, 114 may be any suitable means selected by one of ordinary skill in the art, including, as nonlimiting examples, threaded fasteners, rivets, pins, and the like.

A linear distance between the first fastener 112 and a bend in the main body 102 defining a transition between the major portion of the first arm 103 and the first free end 108 may be greater than a length of the first roller 104. Likewise, a linear distance between the second fastener 114 and a bend in the main body 102 defining a transition between the major portion of the second arm 105 and the second free end 110 may be greater than a length of the second roller 106. It should be appreciated that, in operation, this provides a gap 135 (shown in FIG. 4) between the end of the first roller 104 proximal the first fastener 112 and the first fastener 112, and a gap 137 (shown in FIG. 5) between the end of the second roller 106 proximal the second fastener 114 and the second fastener 114, thereby militating against an undesirable contacting and friction with the first and second fasteners 112, 114 that would otherwise militate against the free rotation of the rollers 104, 106.

Figures 8, 9A, 9B:
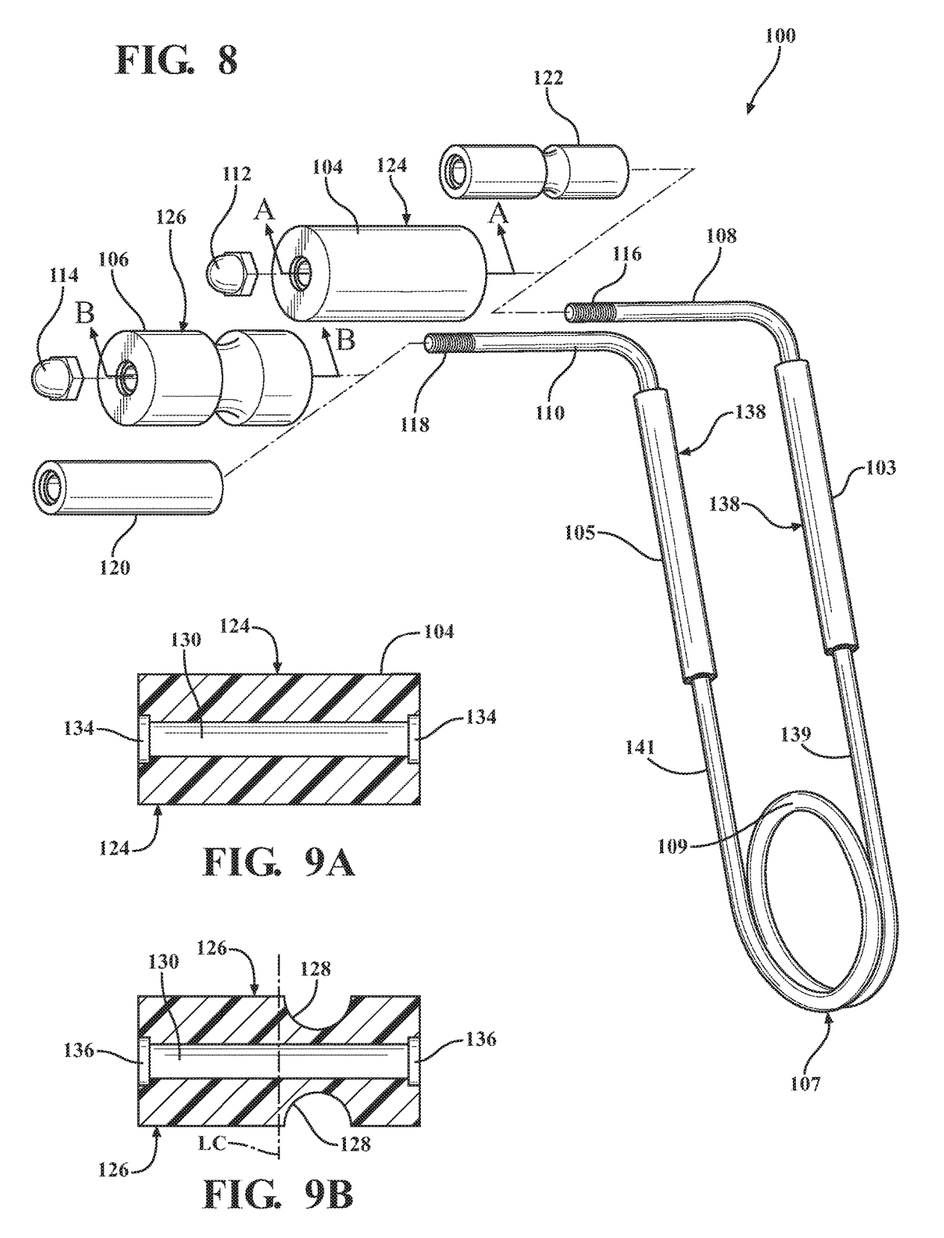
FIG. 8 is an exploded side perspective view of the tube stripping device shown in FIG. 1, further illustrated with an additional set of rollers, and further depicted with a portion of a rubberized grip removed to show an underlying spring portion of the tube stripping device.
FIG. 9A is a cross-sectional front elevational view taken at section line A-A in FIG. 8, and showing another one of the rollers used with the tube stripping device shown in FIG. 1, the roller having an uninterrupted circumferential outer surface and annular recesses formed in ends thereof.
FIG. 9B is a cross-sectional front elevational view taken at section line B-B in FIG. 8, and showing one of the rollers used with the tube stripping device shown in FIG. 1, the roller having a curvilinear recess or channel formed therein around a circumferential surface of the roller and annular recesses formed in ends thereof.

In a most particular embodiment, as shown in FIG. 8, the first roller 104 may be removably attached to the first free end 108 of the first arm 103 of the main body 102, and the second roller 106 may be removably attached to the second free end 110 of the second arm 103 of the main body 102. For example, the first and second free ends 108, 110 may have threaded exterior portions 116, 118 that are configured to cooperating with thread inner portions (not shown) of the first and second fasteners 112, 114. Advantageously, the removability of the first and second rollers 104, 106 allows for a rapid and efficient interchange of the first and second rollers 104, 106 with third and fourth rollers 120, 122, as shown in FIG. 8, which may be sized so as to accommodate differently sized tubing 200 for stripping in operation. Other suitable means permitting for a rapid and efficient replacement of one set of rollers 104, 106 with another set of rollers 120, 122 may also be employed within the scope of the disclosure.

Referring now to FIGS. 9A and 9B, the first and second rollers 104, 106 are generally cylindrical in shape. It should be further appreciated, however, that the first roller 104 and the second roller 106 may have different profiles, which when used together in the stripping position, are effective in more efficiently stripping the tubing 200 in operation. For example, as shown in FIG. 9A, the first roller 104 may have an uninterrupted outer circumferential surface 124. The interrupted outer circumferential surface 124 profile may be one of flat (as shown in FIG. 9A) and convex (not shown) in cross section. For example, as shown in FIG. 9B, the second roller 106 may have an interrupted outer circumferential surface 126 with a groove 128 that is formed therein. In particular examples, the groove 128 is defined by a continuous and uninterrupted curvilinear surface, which does not have any planar portions. Due to the absence of such planar portions, an imparting of undesirable localized stresses on the tubing 200, which might otherwise affect longevity and durability of the tubing 200 long term, is minimized.

Where used together, the outer circumferential surface 124 of the first roller 104 may force the tubing 200 into the groove 128 on the second roller 106. The groove 128 on the second roller 106 together with the circumferential surface 124 of the first roller 104 secures the tubing 200 in place, while rolling the tube stripping device 100 along a length of the tubing 200 in operation.

As also shown in FIG. 9A and FIG. 9B, each of the rollers 104, 106 may have a hollow cavity 130, 132. The hollow cavity 130, 132 is configured to receive one of the free ends 108, 110 of the arms 103, 105. The hollow cavity 130, 132 has a diameter that is larger than a diameter of the ends 109, 110 which it receives, so that the rollers 104, 106 may be free rotating about the free ends 108, 110. Furthermore, each of the rollers 104, 106 may have annular recesses 134, 136 formed at the ends thereof. Each of the annular recesses 134, 136 is in communication with one of the hollow cavities 130, 132. The diameters of the annular recesses 134, 136 are greater than the diameters of the associated one of the hollow cavities 130, 132. It should be appreciated that the annular recesses 134, 136 may facilitate an easier removable and replacement of different ones of the rollers 104, 106, 120, 122 on the free ends 108, 110 of the main body 102.

In particular, and with renewed reference to FIG. 8, the rollers 104, 106 may be removed from the main body 102 and replaced with other rollers 120, 122 of other sizes in order to accommodate different sizes of the tubing 200. Where a user wishes to replace the rollers 104, 106, the user may simply uncouple and remove the fasteners 112, 114, and exchange one sized roller 104, 106 for another sized roller 120, 122. Once the rollers 104, 106 are replaced, the fasteners 112, 114 are re-secured to the main body 102, locking the new rollers 120, 122 in place for use.

The groove 128 shown in FIG. 9B is formed in the outer circumferential surface 126 at a laterally offset position along a length of the second roller 106 relative to a lateral center line LC of the second roller 106. For instance, a bottommost point of the groove 128 may be laterally to one side or another of the lateral center line LC of the second roller 106 This relative positioning of the groove 128 may advantageously provide for sufficient gripping area adjacent to the groove 128 for handling and replacement of the second roller 106, without having the user touch the groove 128 itself. This results in a more hygienic replacement of the second roller 106 and minimizes an opportunity for infection.

Although the groove 128 is shown in FIG. 9B as being offset from the lateral center line LC, it should be understood that in certain embodiments the groove 128 may instead be laterally disposed at the lateral center line LC in the outer circumferential surface 126. In this manner the groove 128 may bisect the second roller 106 into two sections of equal length.

In a further embodiment, the main body 102 may further include a clamp (not shown). Where employed together with the main body 102, the clamp may be disposed between the rollers 104, 106. The clamp when fastened can secure the main body 102 onto the tubing 200, so the user isn't required to continuously squeeze the main body 102 as the rollers 104, 106 are pulled along the length of the tubing 200.

With renewed reference to FIGS. 1-8 and 10, a portion of the main body 102 may also be provided with gripping means such as a polymeric or rubberized coating 138 or tubular polymer or rubber grips (not shown) or finger-sized push plates (not shown). Where the gripping means is the polymeric or rubberized coating 138, the portion of the main body 102 covered with the polymeric or rubberized coating 138 may include the spring portion 107 (shown in FIG. 8 with the coating 138 removed to reveal the underlying coil 109 and major portions 139, 141 of each of the first arm 103 and the second arm 105). However, the coating 138 may not be disposed on the free ends 108, 110 that receive the rollers 104, 106, so as to not interfere with the free rolling of the rollers 104, 106 on the free ends 108, 110 of the arms 103, 105. Such gripping means may facilitate a secure holding and manual squeezing of the main body 102 by the user.

In operation, and as shown in FIG. 10, the medical tubing 200 such as a drainage tube is placed between the rollers 104, 106. The operator then squeezes the main body 102, which compresses the rollers 104, 106 against the tubing 200, while rolling the tube stripping device 100 along the length of the tubing 200. The main body 102 is gripped with sufficient force to strip any debris or excess fluid out of the tubing 200. After cleaning the tubing 200, thusly, the main body 102 is released, thereby disengaging the rollers 104, 106 from the tubing 200.

Advantageously, the tube stripping device 100 of the present disclosure has been found to strip or clean the medical tubing 200 quickly and effectively. Moreover, the tube stripping device 100 is simple to use and minimizes a risk of infection, particularly by disposing the hand of the user operating the tube stripping device 100 into an orientation that is not in-line with the direction of movement of the first and second rollers 104, 106 during the tube stripping operation, From the foregoing description, one ordinarily skilled in the art can easily ascertain the essential characteristics of this invention and, without departing from the spirit and scope thereof, can make various changes and modifications to the invention to adapt it to various usages and conditions.

What is claimed is:

1. A tube stripping device, comprising:
    a main body having a closed end and an opened end, the main body including a first arm, a second arm, and a spring portion, the first arm and the second arm connected to and extending outwardly from the spring portion, the first arm and the second arm selectively and manually movable relative to each other from a spaced apart default position to a stripping position, the spring portion biasing the first arm and the second arm apart and to the default position where not manually moved to stripping position; and
    a pair of free rotating rollers including a first roller and a second roller, the first roller rotatably disposed on a first free end of the first arm, and the second roller rotatably disposed on a second free end of the second arm, the first roller oriented generally parallel with the second roller, the first roller having an uninterrupted outer circumferential surface, and the second roller having an outer circumferential surface with a groove formed therein,
    wherein the groove of the second roller is offset from a lateral center of the second roller.

2. The tube stripping device of claim 1, wherein the first roller is oriented on a first axis and a major portion of the first arm is oriented on a second axis, the first axis being transverse to the second axis and defining an obtuse angle.

3. The tube stripping device of claim 2, wherein the obtuse angle is between 90° and 130°.

4. The tube stripping device of claim 3, wherein the obtuse angle is about 110°.

5. The tube stripping device of claim 1, further comprising a polymeric coating disposed on at least one of the first arm and the second arm of the main body.

6. The tube stripping device of claim 5, wherein the polymeric coating is further disposed on the spring portion of the main body.

7. The tube stripping device of claim 5, wherein the polymeric coating is not disposed on the first free end of the first arm and the second free end of the second arm.

8. The tube stripping device of claim 1, wherein the spring portion includes at least one coil.

9. The tube stripping device of claim 1, each of the first roller and the second roller has a hollow cavity extending therethrough, the hollow cavity of the first roller receiving the first end of the first arm, and the hollow cavity of the second roller receiving the second end of the second arm.

10. The tube stripping device of claim 9, wherein each of the first roller and the second roller has a first end and a second end, each of the first and second ends having an annular recess formed therein, the annular recess in communication with the hollow cavity.

11. The tube stripping device of claim 10, wherein the annular recess has a diameter greater than a diameter of the hollow cavity.

12. The tube stripping device of claim 1, further comprising a first fastener disposed at the first free end of the first arm and a second fastener disposed at the second free end of the second arm.

13. The tube stripping device of claim 12, wherein a distance between the first fastener and a bend in the main body defining a transition between a major portion of the first arm and the first free end is greater than a length of the first roller, and a distance between the second fastener and a bend in the main body defining a transition between a major portion of the second arm and the second free end is greater than a length of the second roller.

14. The tube stripping device of claim 12, wherein the first fastener is removably attached to the first free end and the second fastener is removably attached to the second free end to permit for a manual replacement of the first roller and the second roller.

15. The tube stripping device of claim 14, wherein each of the first free end of the first arm and the second free end of the second arm has external threads, and each of the first fastener and the second fastener has internal threads, the external threads cooperating with the internal threads to selectively secure the first fastener to the first free end and the second fastener to the second free end.

16. The tube stripping device of claim 1, wherein the groove of the second roller has a curvilinear surface.

17. The tube stripping device of claim 16, wherein the curvilinear surface is uninterrupted and does not have any planar portions.

18. A tube stripping device, comprising:
a main body having a closed end and an opened end, the main body including a first arm, a second arm, and a spring portion, the first arm and the second arm connected to and extending outwardly from the spring portion, the first arm and the second arm selectively and manually movable relative to each other from a spaced apart default position to a stripping position, the spring portion biasing the first arm and the second arm apart and to the default position where not manually moved to stripping position;
a pair of free rotating rollers including a first roller and a second roller, the first roller rotatably disposed on a first free end of the first arm, and the second roller rotatably disposed on a second free end of the second arm, the first roller oriented generally parallel with the second roller, the first roller having an uninterrupted outer circumferential surface, and the second roller having an outer circumferential surface with a groove formed therein, wherein the groove of the second roller is offset from a lateral center of the second roller and, the first roller is oriented on a first axis and a major portion of the first arm is oriented on a second axis, the first axis being transverse to the second axis and defining an obtuse angle, and wherein the obtuse angle is between 90° and 130°;
a pair of fasteners including a first fastener disposed at the first free end of the first arm and a second fastener disposed at the second free end of the second arm; and
a polymeric coating disposed on each of the first arm and the second arm of the main body, and the polymeric coating is further disposed on the spring portion of the main body but not disposed on the first free end of the first arm and the second free end of the second arm.

19. A tube stripping device, comprising:
a main body having a closed end and an opened end, the main body including a first arm, a second arm, and a spring portion, the first arm and the second arm connected to and extending outwardly from the spring portion, the first arm and the second arm selectively and manually movable relative to each other from a spaced apart default position to a stripping position, the spring portion biasing the first arm and the second arm apart and to the default position where not manually moved to stripping position;
a pair of free rotating rollers including a first roller and a second roller, the first roller rotatably disposed on a first free end of the first arm, and the second roller rotatably disposed on a second free end of the second arm, the first roller oriented generally parallel with the second roller, the first roller having an uninterrupted outer circumferential surface, and the second roller having an outer circumferential surface with a groove formed therein, wherein the groove of the second roller is offset from a lateral center of the second roller; and
a pair of fasteners including a first fastener disposed at the first free end of the first arm and a second fastener disposed at the second free end of the second arm,
wherein a distance between the first fastener and a bend in the main body defining a transition between a major portion of the first arm and the first free end is greater than a length of the first roller, and a distance between the second fastener and a bend in the main body defining a transition between a major portion of the second arm and the second free end is greater than a length of the second roller, and
wherein the first fastener is removably attached to the first free end and the second fastener is removably attached to the second free end to permit for a manual replacement of the first roller and the second roller, and each of the first free end of the first arm and the second free end of the second arm has external threads, and each of the first fastener and the second fastener has internal threads, the external threads cooperating with the internal threads to selectively secure the first fastener to the first free end and the second fastener to the second free end.

* * * * *